United States Patent [19]

Martin et al.

[11] Patent Number: 4,656,272

[45] Date of Patent: Apr. 7, 1987

[54] PREPARATION OF S-TRIAZINE DERIVATIVES

[75] Inventors: Roland Martin, Ludwigshafen; Lothar Janitschke, Kleinniedesheim, both of Fed. Rep. of Germany

[73] Assignee: BASF Aktiengesellschaft, Ludwigshafen, Fed. Rep. of Germany

[21] Appl. No.: 855,383

[22] Filed: Apr. 24, 1986

[30] Foreign Application Priority Data

May 24, 1985 [DE] Fed. Rep. of Germany ....... 3518670

[51] Int. Cl.$^4$ .......................................... C07D 251/70
[52] U.S. Cl. ................................................... 544/197
[58] Field of Search ......................................... 544/197

[56] References Cited

U.S. PATENT DOCUMENTS 4,402,907 9/1983 Clark .................................. 544/197

FOREIGN PATENT DOCUMENTS 87098 8/1983 Fed. Rep. of Germany ...... 544/197

Primary Examiner—John M. Ford
Attorney, Agent, or Firm—Oblon, Fisher, Spivak, McClelland & Maier

[57] ABSTRACT s-Triazine compounds which can be used as sunscreen agents are prepared in a technically simpler manner by a process in which an ester of a branched alkanoic acid with a saturated aliphatic alcohol or, if appropriate, a mixture of such alcohols is used as the solvent in the reaction of a cyanuric halide with a p-aminobenzoate.

3 Claims, No Drawings

PREPARATION OF S-TRIAZINE DERIVATIVES

The present invention relates to a process for the preparation of s-triazine compounds, which can be used as sunscreen agents, by a technically simpler method.

German Laid-Open Application DOS 3,206,398 describes s-triazine derivatives which are substituted by radicals of p-aminobenzoates and are extremely good sun screen agents. According to the preparation examples, the compounds are obtained by reacting cyanuric chloride with a p-aminobenzoate in a relatively large amount of an aliphatic or aromatic hydrocarbon, in particular gasoline or xylene, as a solvent. Since the desired compounds are obtained from these solvents only in very finely crystalline form, considerable technical problems are encountered in the subsequent filtration, which may take several days. Furthermore, the solvent residues remaining in the end product, and amounting to about 20–30% by weight, have to be removed completely by careful drying under reduced pressure. This drying procedure consumes energy and is very time-consuming; if the compounds are dried too rapidly at too high a temperature, the pure product obtained has a lower solubility in the oils usually used in the cosmetics industry.

It is an object of the present invention to provide a technically very simple process for the preparation of the stated s-triazine derivatives, by means of which the desired sunscreen agents are obtained industrially on a large scale in high purity and in the same or even higher yield, and the time-consuming filtration and removal of hydrocarbon residues are avoided as far as possible.

We have found that this object is achieved if esters of a branched alkanoic acid of 6 to 10 carbon atoms with a saturated aliphatic alcohol of 10 to 20 carbon atoms or with a mixture of such alcohols are used as solvents in the preparation of s-triazine derivatives by reacting a cyanuric halide with a p-aminobenzoate which contains, as the ester alcohol radical, alkyl of 6 to 12 carbon atoms.

Suitable branched alkanoic acids from which the esters used as solvents are derived are those of 6 to 10 carbon atoms, for example 3,5,5-trimethylpentanoic acid or 3,5,5-trimethylhexanoic acid (isononanoic acid). 2-Ethylhexanoic acid is particularly preferred.

Suitable ester alcohols are natural or synthetic, saturated, straight-chain or branched aliphatic alcohols of 10 to 20, preferably 12 to 18, carbon atoms, in particular fatty alcohols, such as lauryl alcohol, palmityl alcohol, cetyl alcohol or stearyl alcohol. These may be in the form of natural mixtures or industrial mixtures obtained in the synthesis, in particular mixtures of alcohols of 12 to 14, 12 to 18, 6 to 18 or 16 to 20 carbon atoms.

Solvents which are very particularly preferably used according to the invention are esters of 2-ethylhexanoic acid with cetyl alcohol or stearyl alcohol or with a mixture of the two alcohols.

Examples of cyanuric halides are cyanuric bromide and, preferably, cyanuric chloride.

The p-aminobenzoates are employed in an amount of 3 moles per mole of cyanuric halide.

Examples of p-aminobenzoates are the esters of p-aminobenzoic acid with a saturated, straight-chain or branched aliphatic alcohol of 6 to 12, preferably 8 to 10, carbon atoms.

Specific examples are 2-ethylhexyl, n-hexyl, 3,5,5-trimethylpentyl, 3,5,5-trimethylhexyl, n-octyl, tetrahydrogeranyl, n-decyl and n-dodecyl p-aminobenzoate.

The amount of solvent to be used according to the invention is preferably from 30 to 60% by weight, based on the weight of the starting compounds.

The reaction is carried out at elevated temperatures of from 100° to 250° C. preferably from 130° to 200° C.

The hydrogen chloride formed during the reaction is advantageously removed from the solution by means of a stream of nitrogen. After the end of the reaction, which can readily be monitored by thin layer chromatography, steam is generally passed through the reaction solution at from 150° to 180° C. for a further 1–2 hours in order completely to remove residual hydrochloric acid and unconverted cyanuric halide and any by-products formed. The mixture obtained contains the desired s-triazine derivative in pure form. It solidifies to a glassy mass, which has the advantage that it can easily be powdered for further processing.

The present invention accordingly relates to a process for the preparation of s-triazine derivatives of the formula (I)

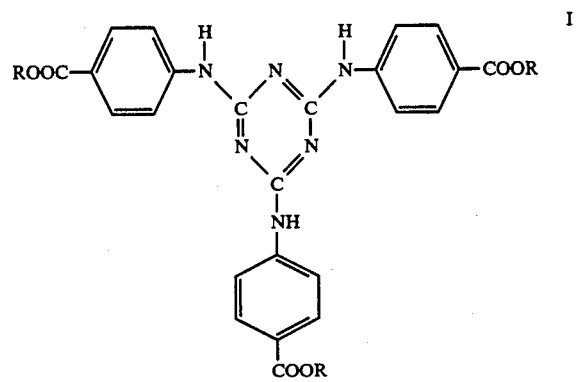

where R is alkyl of 6 to 12 carbon atoms, by reacting a cyanuric halide with a p-aminobenzoate which contains, as the radical of the ester alcohol, alkyl of 6 to 12 carbon atoms, wherein the cyanuric halide is reacted with the p-aminobenzoate in a molar ratio of 1:3 at from 100° to 250° C. in, as the solvent, an ester of a branched alkanoic acid of 6 to 10 carbon atoms with a saturated aliphatic alcohol of 10 to 20 carbon atoms or with, if appropriate, a mixture of such alcohols.

The product obtained is particularly useful in cosmetic formulations, in particular sunscreen agents. The particular advantage of the novel use of the special solvent and of the process according to the invention is that the expensive filtration procedure is omitted. Another surprising advantage is the great increase in yield in the case of the p-aminobenzoates of 6 to 12 carbon atoms, the yield increasing throughout to above 90%, compared with the fluctuating yields of from 50 to 80% in German Laid-Open Application 3,206,398, and the high purity in which the end products are obtained, so that further purification is not necessary. The solvents to be used according to the invention are esters which themselves can be used as cosmetic oils. Hence, they need not be removed after the reaction. The resulting s-triazine derivatives of the formula (I), containing from 25 to 45% by weight of the solvent used according to the invention, can be powdered and screened. The content of 25–45% by weight arises because of the eliminated hydrogen halide and by virtue of the fact that unconverted starting material can be removed completely by the steam distillation.

EXAMPLE 1

1,3,5-Trianilino-p-(carbo-2-ethylhex-1-yloxy)-s-triazine 737 g (3.0 moles) of 2-ethylhexyl p-aminobenzoate and 400 g of an ester of 2-ethylhexanoic acid with a mixture of cetyl and stearyl alcohol were mixed, and the mixture was heated to 100° C. 184.4 g (1.0 mole) of cyanuric chloride were added to the resulting solution, and the mixture was slowly heated further, while stirring. At about 130° C., evolution of hydrogen chloride began. When the initial reaction had died down, the mixture was heated further to an internal temperature of 170° C. The resulting suspension is converted to a clear solution in the course of the subsequent reaction time of 24 hours. The hydrogen chloride formed during the reaction was expelled by means of a gentle stream of nitrogen. When the reaction was complete (monitored by thin layer chromatography), steam was passed through the solution at 170° C. for from 1 to 2 hours in order to remove traces of hydrogen chloride and unconverted starting material. Thereafter, the stirred mixture was cooled to about 130° C. and the liquid contents of the flask were discharged, the contents solidifying to a glassy mass. Comminution gave 1192 g of a fine powder containing 63.5% (determined by HPLC) of 1,3,5-trianilino-p-(carbo-2-ethylhex-1-yloxy)-s-triazine, which corresponded to a yield of 92% of theory.

EXAMPLE 2

1,3,5-Trianilino-p-(carbo-3,7-dimethyloct-1-yloxy)-s-triazine 81.3 g (0.3 mole) of 3,7-dimethyloctyl p-aminobenzoate, 40 g of the ester of 2-ethylhexanoic acid with a mixture of cetyl and stearyl alcohol and 18.4 g (0.1 mole) of cyanuric chloride were mixed together, and the mixture was heated. At about 110° C., evolution of hydrogen chloride began. When the initial reaction had died down, the mixture was heated further to 180° C. and stirred for 42 hours at this temperature. During this procedure, a clear solution formed. When the reaction was complete (monitored by thin layer chromatography), steam was passed through the reaction mixture at 180° C. for a further 2 hours. The mixture was cooled to 100° C., and the liquid contents of the flask were discharged. On further cooling, the material solidified to a glassy mass. 120 g of a powder containing 65% (determined by HPLC) of 1,3,5-trianilino-p-(carbo-3,7-dimethyloct-1-yloxy)-s-triazine were obtained, corresponding to a yield of 86% of theory.

We claim:

1. A process for the preparation of an s-triazine derivative of the formula (I)

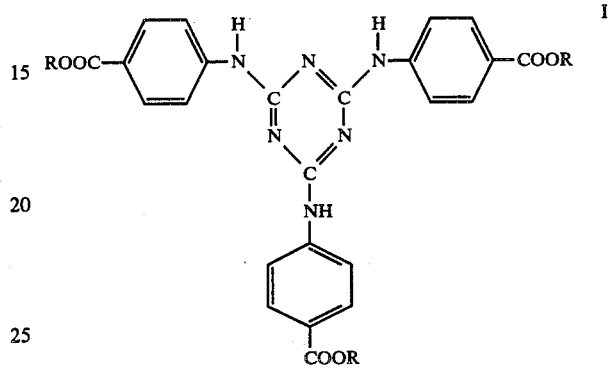

where R is alkyl of 6 to 12 carbon atoms, by reacting a cyanuric halide with a p-aminobenzoate which contains, as the ester alcohol radical, alkyl of 6 to 12 carbon atoms, wherein the cyanuric halide is reacted with the p-aminobenzoate in a molar ratio of 1:3 at from 100° to 250° C. in, as the solvent, an ester of a branched alkanoic acid of 6 to 10 carbon atoms with a saturated aliphatic alcohol of 10 to 20 carbon atoms or with, if appropriate, a mixture of such alcohols.

2. A process as claimed in claim 1, wherein the reaction is carried out in from 30 to 60% by weight, based on the total weight of the starting compounds, of solvent.

3. A process as claimed in claim 1, wherein the reaction is carried out in, as the solvent, 2-ethylhexanoic acid esterified with cetyl or stearyl alcohol or with a mixture of these.

* * * * *